United States Patent [19]

Bori

[11] Patent Number: 4,872,840
[45] Date of Patent: Oct. 10, 1989

[54] DENTAL IMPLANT AND METHOD

[75] Inventor: Jacques E. F. Bori, Watertown, Mass.

[73] Assignee: Team Incorporated, Newton, Mass.

[21] Appl. No.: 73,489

[22] Filed: Jul. 15, 1987

[51] Int. Cl.$^4$ .............................................. A61C 8/00
[52] U.S. Cl. .................................................... 433/173
[58] Field of Search ............... 433/173, 174, 175, 201; 623/16

[56] References Cited

U.S. PATENT DOCUMENTS

| | | | |
|---|---|---|---|
| 3,790,507 | 2/1974 | Hodesh | 433/173 |
| 4,304,553 | 12/1981 | Heimke et al. | 433/173 |
| 4,379,694 | 4/1983 | Riess | 433/193 |
| 4,424,037 | 1/1984 | Ogino et al. | 433/173 |
| 4,440,750 | 4/1984 | Glowacki | 623/16 |
| 4,525,145 | 6/1985 | Schnieher | 437/173 |

FOREIGN PATENT DOCUMENTS 152312  7/1986  Japan ................................. 437/175

Primary Examiner—Robert Peshock
Attorney, Agent, or Firm—Robert K. Tendler

[57] ABSTRACT

A pure titanium implant having tightly captured bone therethrough is provided to dramatically reduce the nuturing period prior to the time that an implant may be utilized, by providing osteointegration or bone growth guided through the implant, in addition to any osseointegration or bone to titanium adhesion. In one embodiment, rings of compacted lyophylised or freeze-dried bone are secured between dove tailed, pure-titanium rings to a central implant shaft to guide bone growth through the implant from one side to the other for improved implant anchoring, without infection or rejection. In another embodiment, the implant includes a pure-titanium body having lateral channels completely through the implant, with bone rigidly secured in the channels to guide bone growth completely through the implant. In a method for implanting, rather than drilling a large hole with a slow-speed drill, a series of small drilled holes create, via osteoclasia, a softened-bone structure into which the implant is forced below bone level after a cavity is prepared by removal of a small amount of softened bone at the implant site. The implant is to be inserted into softened bone structure after two to three weeks and before well advanced mineralization, which occures after one to two months. Upon insertion, the implant is covered with the full thickness flap of gingiva, and the flap is sutured over the implant. A healing period of one to one and a half months secures the implant into position via osteoclasia, osteogenesis, and incipient osseointegration. The site is then reopened and a clinical crown or abutment is fixed to the submerged implant, followed by the placement of a ring of semiporous material to prevent epithelial downgrowth at the submerged implant which interferes with osseointegration. In one embodiment, an implant is provided with a bulbous bottom end for stress relief during insertion and during use. In another embodiment, the implant is dismantleable after removal, to permit the microscopic observation of the healing process. A specialized pulling tool is provided to permit the removal of the superstructure from the abutment for prosthetic purposes. A further pulling device for implant removal includes the replacement of the abutment with a bolt-type crown which permits clamping to the implant and twisting of the submerged portion to remove the tightly secured implant.

33 Claims, 10 Drawing Sheets

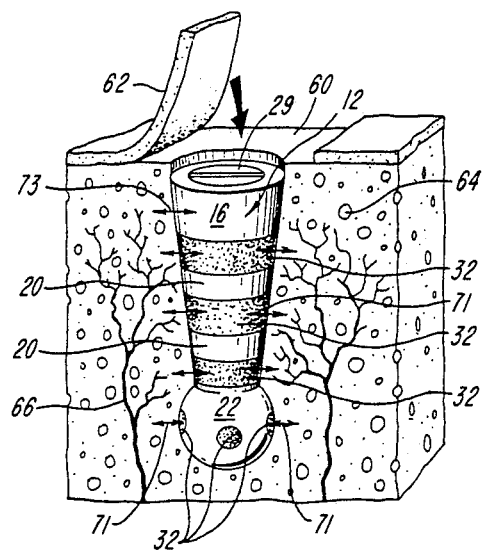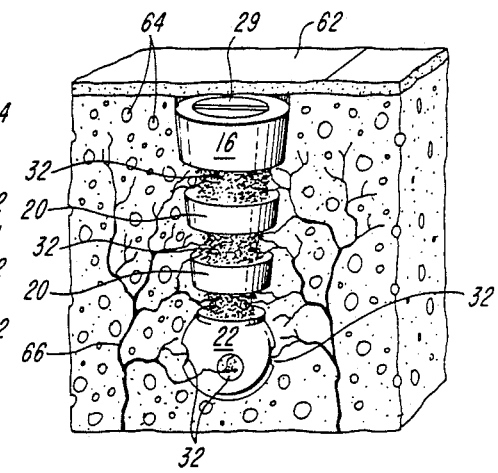
*FIG. 5A*  *FIG. 5B*
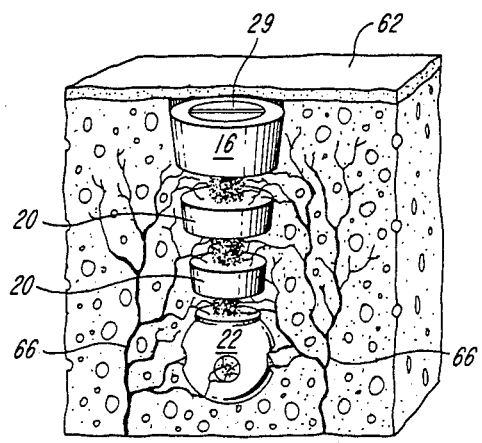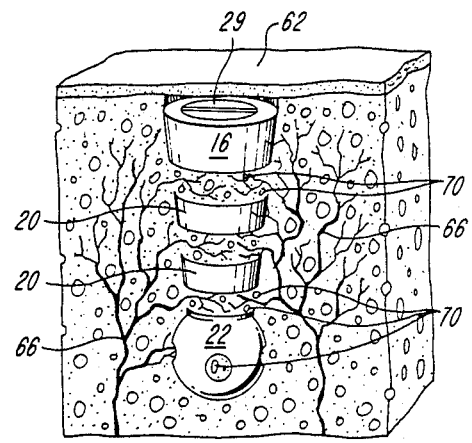
*FIG. 5C*  *FIG. 5D*

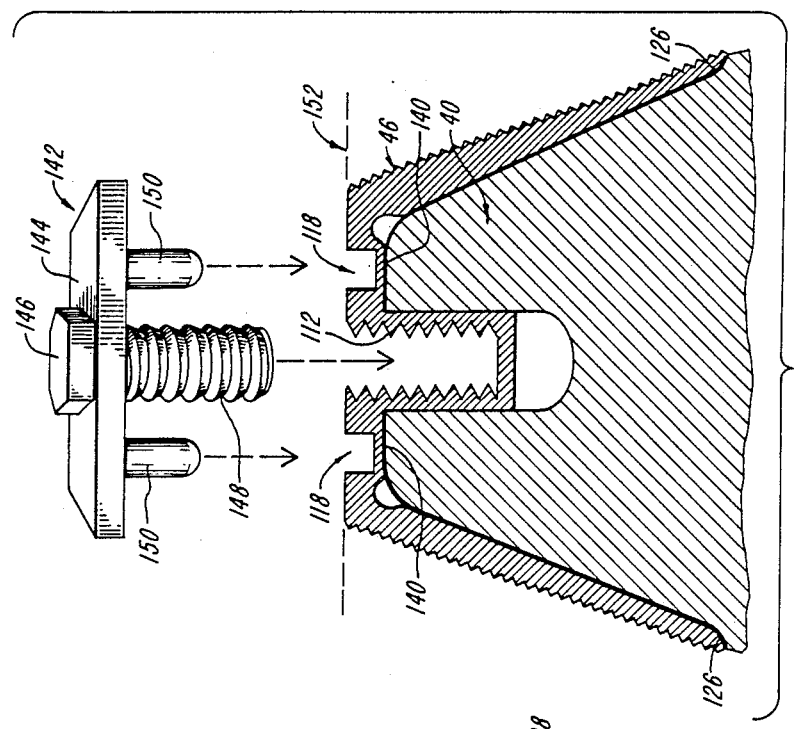
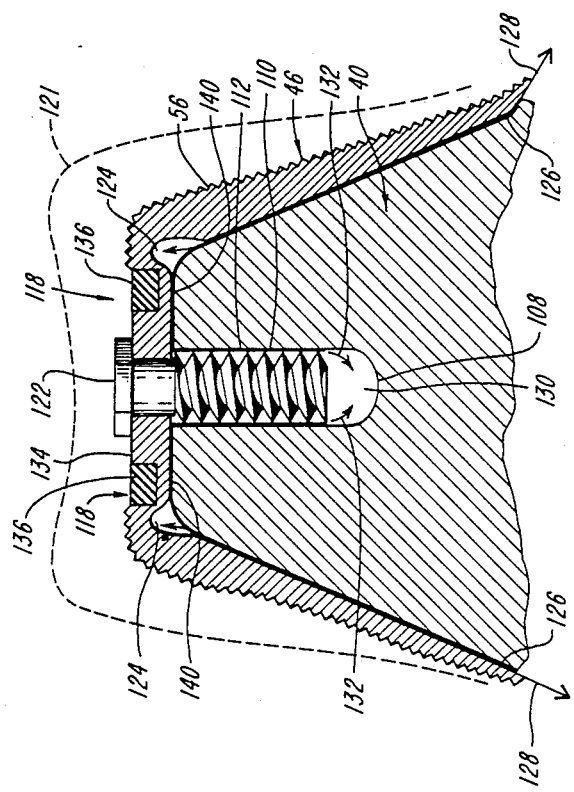
FIG. 9A
FIG. 9B

DENTAL IMPLANT AND METHOD

FIELD OF INVENTION

This invention relates to dental implants and more particularly to a method and apparatus for securing implants.

BACKGROUND OF THE INVENTION

Dental implants consist of metallic, ceramic, or polymeric materials which are placed either on or within the mandibular or maxillary bone to support fixed or removeable prostheses. The function of an implant is to provide an abutment to support and stabilize a prosthesis. Generally an implant is placed in an edentulous area after it is determined that a conventional restorative modality is not satisfactory.

The fundamental problems associated with implant design and application have been: obtaining highly biocompatible materials which withstand the adverse oral environment without corrosion and loss of mechanical properties; designing implant shapes and restorations which provide mechanical support and stabilization for the prosthesis without causing extensive bone resorption; and developing an interlocking between the gingival and mucosal tissues and the implant to retard bacterial penetration and infection in sites where the implant extends into the oral cavity.

Until the so-called Branemark implant, no commercial implant was available for which there was a direct attachment of bone to the surface of the implant via a process called osseointegration. It should be noted that the Branemark implant is a pure titanium implant in which osseointegration can be produced. However, the Branemark implant requires a six month nurturing period. As will be seen, the subject system reduces this healing period to as little as one month by combining osseointegration with osteogenesis or osteointegration, in which new bone is guided directly through the implant.

Note that the implant must be stabilized immediately after placement and must be free of any movement during the healing process. Movement causes formation of a connective tissue interface between bone and implant. This connective tissue provides a flexible cushion and subsequent mobility. Where there is implant mobility, epithelial invagination, and implant failure often occur. As will be seen, the subject system immobilizes the implant during a greatly reduced nurturing period due to its unique pure titanium/captured-bone operation, as well as a new procedure specified for implantation involving multiple high or low speed drilled holes accomplished by water cooling.

More particularly, the main problem with the Branemark implant is that Branemark wishes to obtain osseointegration between the bone and pure titanium. Osseointegration as defined herein means the binding of bone to some foreign material such as pure titanium. While it has been found by Branemark that such osseointegration can in fact occur with pure titanium, the problems are two fold. The first problem is that osseointegration, if it occurs at all, occurs sufficiently only after a six month nurturing period. Secondly, osseointegration may never occur to a sufficient degree to stabilize the implant no matter what time period is utilized.

Other problems include the utilization of any type of sharp edges or screws without any captured bone mechanism for osteointegration which can result in inflammation without subsequent new-bone growth. Moreover, with the utilization of the Branemark equipment there is a problem of the cost of the drilling apparatus which must be slow speed, as well as requiring the exact matching of the drilling diameter to the diameter of the implant, which even if exact, is nonetheless conducive to bone remodelling. Hence, there is a lack of an exact fit because the bone tissue is alive and will react osteoclastically to any kind of surgical procedure.

Note, one of the most important factors with respect to the Branemark or any other implant which utilizes interstices, indents, or other types of orifices, in which bone is to grow is that it is necessary to stimulate bone growth into these interstices, a situation which does not often occur absent the utilization of immobile tightly packed cortical bone within the implant itself which is part of the Subject Invention.

By way of further background, implant systems are illustrated in U.S. Pat. Nos. 3,609,867; 4,277,238; 3,789,029; 3,918,100; 3,790,507; 3,606,615; 4,244,689; 4,131,597; 4,141,864; 4,547,390; 4,595,713; and 4,202,055. In these patents various bone compositions have been utilized to aid artificial bone grafting both in the dental field and in other fields.

One patent in particular, U.S. Pat. No. 4,600,388, indicates an implant with loosely held bone material. One of the problems with the utilization of such loosely held bone material is the movement or migration of the unclamped bone during the healing process which prevents the bonding of bones to the implant. Moreover, any bone-to-implant bonding would occur over dramatically long periods of time or will not occur at all. In other words, loosely-packed particles can prevent bone formation over long distances because of the formation of dense connective tissue surrounding the bone particle.

Additionally, one of the aforementioned patents, U.S. Pat. No. 4,244,689, illustrates an endosseous plastic implant with holes adapted to promote bone growth therein. Note that no bone material is initially placed in the shallow indents and that any bone that grows into the indents is strictly a chance happening which cannot be guaranteed. Moreover, the shallowness of the intercuts does not afford much fixative power. Also because of the dielectric constant of the plastic, no electric charge stimulation occurs to promote bone formation.

Further, in addition to the above-mentioned patents, a pure titanium basket structure made by Friedrichsfeld is utilized for implants in which a relatively large hole is drilled in the mandibular bone, with the basket being utilized to permit bone growth therethrough. However, the basket does not initially carry any bone, such that bone growth is chancy without such positive stimulation. Moreover, the Friedrichsfeld implant can fail because of bacterial ingrowth.

It will be noted that none of the above references cite the utilization of bone which is immobilized or rigidly held in a pure titanium structure, in which the tightly held bone runs completely through the structure to promote ankylosis or bone-to-bone adhesion, blood vessel growth and consequent bone growth guided completely through the implant. It is important in the final stabilization of the implant that the bone growth be promoted completely through the implant and this cannot be accomplished through loose bone particles in a container or merely through the utilization of indents in the surface of an implant or channels therethrough.

As mentioned hereinbefore, for those implants which require drilling, the drills utilized are generally of a diameter equivalent to that of the proposed implant. These drills, aside from being low speed and extremely expensive, do not result in perfect adaption of the implant to the bone on a timely basis unless nurtured for six months, this assuming that the drill hole perfectly matches the implant morphology and that the bone did not react excessively in an osteoclastic manner. If not, then a dense connective tissue capsule forms, preventing bone-to-implant bond or osseointegration.

Most importantly, in all previous implant techniques, the healing process necessary before the implant can be capped with a usable tooth is on the order of six months, a time period in which the patient is deprived of even temporary tooth structure.

SUMMARY OF INVENTION

In contradistinction to the above-mentioned techniques, in one embodiment, the subject implant is made of pure titanium which clamps interstitial cortical or dense bone or bone particles in rings or channels that preferably go laterally from one side of the implant to the other, thereby to promote bone growth completely through the implant structure. Preferably, the bone particle size is as small as possible without causing bone dissolution, to present greater surface area for bone growth, to provide good packing efficiency, and to provide larger numbers of flow channels through the implant. In one embodiment, the bone particle size is greater than 200 microns.

Secondly, the implant has a bulbous bottom end for stress relief.

Thirdly, a new surgical technique is provided at the implant site for better implanting in which the implant is pushed into softened bone produced by surgically-induced osteoclasia. This may be provided through the utilization of thin high-speed drills and water coolant, with the drilling pattern being a conical pattern of holes running down through the alveolar bone. After three to five weeks depending on the bone density, these holes provide a mushy, softened-bone structure through which the implant can be pushed into position.

A fourth inventive feature is below-bone implant position to which the implant is pushed. The reason for insertion below bone level is to counteract an ill fitting relation between the bone and the implant following healing. This is based on the fact that the superficial edges of the bone at the recipient site will be lost via surgical trauma. Insertion below these lost superficial edges insures a perfect fit at the top of the implant whatever technique for recipient site preparation is used.

Therefore, there is no need to size the drill to the particular implant. Moreover, this implant technique provides immediate sizing as the implant is pushed into the softened bone area. This is true whether or not the implant is made of pure titanium, whether or not it has entrapped bone, or whether or not the end of the implant is bulbous. However, all of the above contribute to increased success of implantation. Note with this method, the healing process is accelerated due to the flow of the surrounding stimulated bone structure with respect to the implant.

The subject system thus cuts down the nurturing period prior to the time that the implant may be utilized for a temporary cap or prosthesis, with the clamped bone of the pure titanium implant providing for ankylosis or fixation of bone-to-bone followed by osteoclasia which is debridement of the bone particles, followed by osteogenesis or osteointegration which is the formation of bone through the implant; all of this as osseointegration occurs. The subject implant thus induces surgical inflammation, osteoclasia, and osteogenesis to tie up the implant to the bone, after which the inflammation recedes without endangering the stability and/or ankylosis or bone-to-bone attachment through the implant. This is because the originally induced inflammation is part of osteogenesis which is the building of bone through the implant. Thus rather than avoiding initial inflammation, it is this inflammation which induces osteogenesis.

The subject structure thus provides not only for an accelerated immobilization of the implant and thus a decrease in the time in which a usable device can be placed in operation, but also results in guided osteogenesis completely through the implant which, due to the utilization of clamped bone within the implant, thus securing the implant via osteogenesis while osseointegration continues.

As a fifth inventive feature, it has also been found that the utilization of a ring of semiporous material to restrain epithelial downgrowth following the insertion of the clinical abutment prevents failure, with the downgrowth of the epithelialization being controlled by the size of the ring or washer which is placed over the abutment once the abutment has been properly positioned.

As a sixth inventive feature, in one embodiment, the abutment protrudes up through a central hole in the ring and the overlying gingival flap so that superstructure may be provided to permit suturing to a notched implant abutment.

As an seventh inventive feature, the cap is easily removed from the abutment through the use of a specialized fixture.

As a eighth inventive feature, in another embodiment, the abutment is removable to permit affixing of a cap designed to aid removal of the implant if needed.

More specifically, in a preferred embodiment, a pure titanium and bone implant is provided to reduce the nurturing period prior to the time that an implant may be utilized. The implant includes a tapered pure titanium implant having either rings or channels filled with bone rigidly secured therein to promote bone growth completely through the implant for improved implant anchoring, without infection or rejection of loosely carried bone fragments. The final osteogenesis in which the initial bone material in the rings or channels is replaced by grown bone guided through the implant by the rings or channels is accompanied by osseointegration involving bone-to-implant adhesion. Osteogenesis is preceded by ankylosis or bone-to-bone attachment which is followed by osteoclasia, or the destruction, debridement, digestion, or dissolution of the bone in the channels by osteoclasis. New bone cells, osteoblasts, will then grow into the channels to provide bone replacement via osteogenesis. The success of the osteogenesis is provided by the presence of the proper cells, e.g. the proper bone cells, adequate vascularization to carry nutrients, and the stimulation triggered by the entire system. The above processes help to affix the implant in as little as one month, as opposed to the usual six month waiting period.

In one embodiment, the implant is provided with a bulbous bottom end, to prevent vertical implant movement due to longitudinal stresses during normal use and also during implantation to move softened bone out of the way so that the implant may be forced in without damage to the surrounding bone, with the surrounding softened bone conforming back over the smaller implant shaft to increase stabilization during healing. Thus, in the subject method of implanting, the bulbous structure spreads the initial stress during implantation, when the implant is pushed through soft bone left by a series of small diameter holes drilled in a conical configuration down through the bone in the area of the implant. These holes after approximately fifteen days provide a mushy or softened bone consistency of cortical bone fragments and blood vessels at the position at which the implant is to be inserted. Upon provision of a softened bone area, the implant is inserted and covered with a gingival flap for an initial nurturing period of a month. Following initial healing, a re-entry procedure is performed in which a flap is lifted, unveiling the submerged implant portion from which a plastic screw is removed. The clinical crown or abutment is then affixed in position. A semiporous filter washer then is sleeved onto the crown adjacent to and onto the bone structure. The flap is then sutured in position, with a hole in the flap allowing for the protrusion of the clinical crown or abutment through the flap.

Trapped between the clinical crown and the submerged portion of the implant, the above-mentioned ring has a diameter of sufficient size to ensure that downgrowth of the epithelium will not occur between the host bone and the implant during the healing period. In one embodiment, this membrane is between 8 and 15 millimeters in diameter depending upon the size of the implant. The size of the ring determines the time before epithelial downgrowth, which downgrowth can be limited to up to 40 days, by which time the progress of acceptance of the implant can be evaluated and the ring or washer removed. An alternative to the utilization of a microporous ring or washer is the use of resorbable material.

In one embodiment, the implant is made of a sandwich structure which is through-bolted and in which in between the sandwiched pure titanium parts are rings of sterilized bone particles, with the sandwich structure capturing the bone so that it is rigidly retained which prevents bone mobility during the healing process. An alternative one-piece configuration is possible for the pure titanium/bone implant, with the bone being captured in through-holes both at the shaft and through the bulb at the end. However, the above-mentioned sandwich structure permits dove tailed clamping of the bone to the implant which prevents bone migration. This is because the bone is mechanically sandwiched or held in dove tailed grooves, with the sandwich structure also permitting dismantling of the implant for histologic study. In a further embodiment, the implant is of solid pure titanium with no bone but with a shank and a bulbous end. It will also be understood that sputtered bone may be used over the implant structure in conjunction with the pure titanium/bone structure itself.

It will thus be appreciated that the use of dense bone or cortical bone in the implant channels stimulates ankylosis and that should the implant take, its retention is assured over greater stresses and for longer periods of time than heretofore possible. The process also eliminates the problem of exact sizing for drills or the use of slow-speed drills.

In one embodiment, the clinical crown is made with crossed grooves on the occlusal surface to hold and locate sutures and superstructures for the build up of the final prosthesis. Thus within one month after the initial implantation, the patient may chew with the utilization of a temporary device.

In summary, a pure titanium implant having tightly captured bone therethrough is provided to dramatically reduce the nurturing period prior to the time that an implant may be utilized, by providing both osseointegration and osteogenesis. In one embodiment, rings of compacted lyophylised or freeze dried bone are secured between dove tailed, pure-titanium rings to a central implant shaft to guide bone growth effectively through the implant from one side to the other. This provides for improved implant anchoring, without infection or rejection associated with loosely carried bone fragments. In another embodiment, the implant includes a pure-titanium body having lateral channels completely through the implant, with bone rigidly secured in the channels to guide bone growth completely through the implant.

The final osteogenesis in which the initial bone material in the implant is replaced by grown bone guided through the implant by the channels or rings of bone is accompanied by osseointegration involving bone-to-titanium implant adhesion. First ankylosis occurs about the bone rings which tightens the implant in position. This is followed by osteoclasia or dissolution of the bone in the rings or channels accompanied by osteogenesis resulting in bone replacement. Hence osteointegration and osseointegration go hand in hand.

In a method for implanting, rather than drilling a large hole with a slow-speed drill, a series of small, high-speed drilled holes using a water cooling device create, via osteoclasia, a softened bone structure into which the implant is forced after cavity preparation. The implant is to be inserted after two to three weeks and before well advanced mineralization, which occurs after one to two months. Upon insertion, the implant is covered with a full thickness flap of gingiva, and the flap is sutured over the implant. A healing period of one to one and one half months secures the implant into position via osteoclasia, osteogenesis and incipient osseointegration. The site is the reopened and a clinical crown or abutment is affixed to the submerged implant followed by the placement of a ring or semiporous material to prevent epithelial downgrowth at the submerged implant which interferes with osseointegration.

In one embodiment, the implant is provided with a bulbous bottom end for stress relief during insertion and during use. In another embodiment, the implant, once removed, is dismantleable to permit the microscopic observation of the healing process. A specialized pulling tool is provided to permit the removal of the superstructure from the abutment for prosthetic purposes. A further pulling device for implant removal includes the replacement of the abutment with a bolt type crown which permits clamping to the implant and twisting of the submerged portion of the implant for removal. This type of tooling is important in order to break the implant free of the surrounding bone since there is, in essence, bone invagination through and about the pure titanium structure.

Therefore, it is the purpose of the Subject Invention to create, in one embodiment, an implant composed of pure titanium holding sterilized, organic-bone particles to enhance or speed up the process of implant immobilization by bone-to-bone adhesion through ankylosis, osteoclasia followed by osteogenesis, all of which help to affix the implant within a period of as little as one month as opposed to a six-month period for prior osseointegration, pure-titanium implants. Although it takes up to one year for complete resorption and replacement by the surrounding lining bone, the device is functional for use with a crown, bridgework or other removable appliances within a two-month period after insertion, as osseointegration continues parallelling the induced osteointegration.

BRIEF DESCRIPTION OF THE DRAWINGS

These and other objects of the Subject Invention will be better understood in connection with the Detailed Description taken in conjunction with the Drawings of which:

FIGS. 5A–5D illustrate in cross section and diagrammatically the initial process of implanting the subject implant, in which FIG. 5A illustrates the initial implantation of the implant structure within the softened bone material below the bone level, with FIG. 5B illustrating the covering of the implanted structure with the gingival flap, also illustrating the beginning of ankylosis and osteoclasia; with FIG. 5C illustrating the completion of osteoclasia as osteogenesis proceeds and, with FIG. 5D illustrating the completion of osteogenesis showing the formation of new bone particles through the implant;

FIGS. 9A–9C are cross sectional and diagrammatic illustrations of one embodiment of a system for the removal of the superstructure cemented or otherwise affixed to the abutment or clinical crown without endangering the implant, with FIG. 9A illustrating the positioning of a pulling fixture above the cap, after removal of the acrylic layer and/or ceramic layer, with FIG. 9B illustrating the removal of the rubber or plastic blanks prior to the insertion of the downwardly projecting extensions of the fixture and with FIG. 9C illustrating the dynamic removal of the superstructure from the abutment with the contacting of the extensions with the top surface of the abutment, with the net affect being the pulling out of the superstructure from the abutment; and, FIG. 10 is a diagrammatic illustration of an implant removal system illustrating the utilization of a bolt in lieu of the clinical crown, also illustrating the utilization of a lock washer and illustrating the breaking of the bony invagination within the implant thereby to free up the implant so that the implant may be both rotated and wiggled through the utilization of a suitable forceps-type wrench which may include a vice grip locking type feature.

DETAILED DESCRIPTION

It will be appreciated that the subject implant device, in one embodiment, incorporates osteointegration which is integrating invested bone to live bone, be it bone, stimulated bone, or bone particles. This should be distinguished from osseointegration which is the organical, physical, chemical attachment of live bone to structures other than bone. In the case of Branemark, the structure, referred to is pure titanium in which osseointegration occurs over a period of six months as mentioned hereinbefore. The Subject Invention can involve both the combination of osteointegration through the guiding of new bone through the implant as well as the aforementioned osseointegration if osseointegration take place. It should be noted that while the Subject Invention has been described as a combination of osteointegration and osseointegration, it has been found that osseointegration takes place with such a degree of regularity and predictability that it may or may not be necessary to provide for osseointegration. It should also be noted that while it has been asserted that osseointegration does in fact take place with a great degree of regularity when utilizing a pure titanium implant, this is not a predictable phenomena. Thus, the subject system as it relates to the utilization of the captured bone, results in the immobilization of the implant whether osseointegration occurs or not. Of course, immobilization is increased somewhat if osseointegration does in fact occur.

Figure 1:
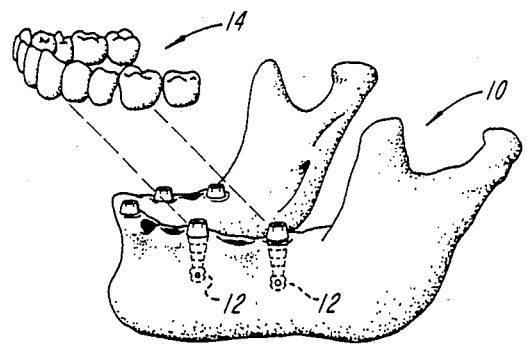
FIG. 1 is a diagrammatic representation of a mandible including implants of the Subject Invention to which a prosthesis is to be secured.

Referring now to FIG. 1 a mandible 10 is provided with implants 12 to which is attached a prosthesis 14 which may be a single crown, a bridged structure covered with acrylic, and/or a ceramic superstructure or a combination of the above. One of the purposes of the subject implant is to assure the ability to attach a superstructure as soon as possible so that the patient can obtain usage of the superstructure in order to chew or for esthetic or other functional purposes.

Figure 2:
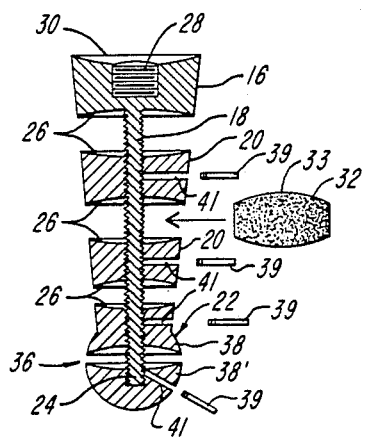
FIG. 2 is a cross sectional and diagrammatic illustration of one embodiment of the subject implant illustrating the utilization of a central unitary screw threaded shaft and surrounding dove tailed rings adapted to secure cortical or densely packed bone therebetween.

Referring now to FIG. 2, in one embodiment, the implant may be of a dove tailed structure in which a unitary top portion 16 is provided with a downwardly projecting screw portion or central implant shaft 18 to which are attached intermediate dove tailed rings 20, with a bulbous structure 22 affixed to the bottom portion 24 of the central shaft structure. The dove tailed rings may be provided with conical surfaces 26 to provide the dove tailing, although dove tailing is not necessary in certain instances depending upon bone clamping efficiency. Alternatively, other types of securing mechanisms may be used to securely affix cortical or dense bone material inbetween the various components of the implant. However, the reason for preferring dove tailing is to promote ingrowth which immobilizes the implant to an even greater extent than thought possible and which increases the surface of the bone ingrowth. It will be appreciated that top 16 is provided with a screw threaded aperture 28, the purpose of which is to anchor an abutment or clinical crown thereto after the implant has been stabilized as will be described hereinafter. The aperture 28 is, in general, provided with a plastic screw 29 shown in FIGS. 5A-5E during the initial period to prevent tissue ingrowth. It should also be noted that the top surface 30 of the top of the implant may be conical to retard tissue downgrowth during stabilization. This prevents cells from growing down across the top portion of the implant. The conical top portion of the implant also more tightly secures a mating abutment due to the conical mating structure. This also prevents breakage of the clinical crown from the top portion of the implant.

It can be seen that the implant 12 is provided with rings 32 of compact bone having central bores 33, which rings are secured in position not only between dove tailed rings 20 of the implant and between the upper ring and top portion 16, but also within channels 36 within the bulbous portion 22 of the implant. These channels are provided by a split sphere type structure illustrated by sphere halves 38 and 38'.

As will be described in connection with FIG. 7 the implant may be of a unitary structure having a through-hole structure which contains the dense bone. The bone may be held in place either by virtue of extremely dense initial packing or through any compatible adhesive. The capturing of the bone is so that osseointegration can occur rather than being prevented by loose bone particles.

With respect to the type of bone which may be utilized either in ring form or compacted through holes or orifices within the titanium implant, it will be appreciated that cortical or freeze-dried bone can be packed in such a manner. Other types of bone material are the patients own dentin and/or cortical bone chips. It will be further appreciated that the entire overstructure may contain a thin layer of sputtered bone to aid in the retention of the packed bone and to continue the process of osteointegration prior to osseointegration which might occur at some site within the confinement of the bone rings in contact with the pure titanium.

Note that all parts mounted on screw portion 18 may be secured to the screw portion by set screws 39 in channels 41.

STRESS RELIEF BULB

It will be appreciated that the stress relief bulb may be utilized with a variety of different implants and implant structures to provide the aforementioned stress relief. Thus the bulb may be utilized with the implant structure described herein or with other types of implants for stress relief. As will be described hereinafter, the bulb also serves the purpose of parting the spongy bone tissue provided by a procedure described in connection with FIGS. 4A-4C.

It will be appreciated that should the Branemark type device be provided with a bulbous stress relief end, this stress relief end portion will aid in the expected osseointegration which is dependent on perfect immobilization of the implant for the duration of six months in the aforementioned Branemark process. Moreover, while, in the illustrated embodiments, the bulb diameter is greater than that of the shaft due to the use of tapered shafts, the shaft itself can be straight with an enlarged rounded end being provided to the base of the shaft, which rounded end may be either completely rounded or bullet shaped, but certainly not pointed or sharpened which would defeat the purpose of the stress relief. It will be appreciated that the aforementioned basket structure implant provides for a rounded end, but the diameter of the basket structure and the end are the same. Thus, the stress relief provided by this rounded end is insufficient for stabilization purposes.

In summary, the bulbous end provides stress relief against vertically oriented chewing and/or para-function. Not only are the downward stresses relieved by the bulbous structure but also upwardly directed forces are opposed by the top surface of the bulbous structure.

ABUTMENT

Figure 3:
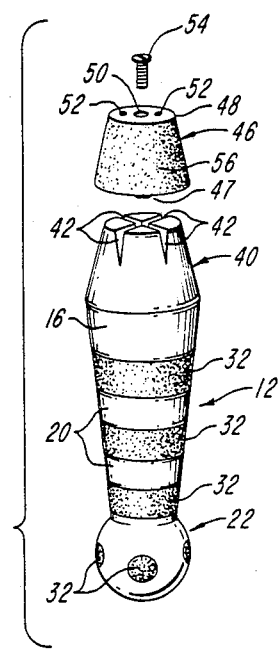
FIG. 3 is an exploded view and diagrammatic illustration of the implant of FIG. 2, illustrating the utilization of rings of dense packed cortical bone, also illustrating the utilization of an abutment on top of the implant and the removeable cap which is to be secured to the abutment or clinical crown.

Referring to FIG. 3, as can be seen a clinical crown or abutment, generally indicated by reference character 40 is affixed to top portion 16 of implant 12, with the abutment being of a frustoconical configuration, and having, in one embodiment, crossed slots 42 in the top surface thereof. These crossed slots serve two purposes as will be seen. One of these purposes is for optional suturing of the completed implant during a further healing period as will be described in connection with FIG. 5L. More importantly, however, the slots in the top portion of the abutment are utilized to mate with ribs (not shown in this figure) of cap 46, which is slipped over and fixedly attached to abutment 40 by cement and/or mechanical means such as illustrated by a pin or screw 47 affixed to and depending from the base of the cap.

For purposes which will be described later, cap 46 is provided with a top surface 48 having a threaded aperture 50 and pin receiving apertures 52, with aperture 50 being provided with a plastic screw 54 at the top portion thereof. The purpose of the threaded aperture 50 and pin receiving apertures 52 is to provide for the removal of the cap from the abutment when the prosthesis is to be re-vamped or otherwise re-fitted.

It will be appreciated that in a preferred embodiment, the structures involved are made of pure titanium, which means that not only is the initial implant made of pure titanium but also the abutment and the cap. It will also be noted that the exterior surface 56 of the cap is serrated, such that superstructure can be easily attached thereto by virtue of cementing or other adhesive or mechanical press fit means. What will be apparent, whether or not pure titanium is utilized as the metal for the implant and superstructure, it is important that the metals be the same so as to prevent electrolysis with the saliva acting as the electrolytic agent. While the Subject Invention is not limited to pure titanium as a metal, it has been found that pure titanium is the only material presently known for which osseointegration may occur.

ENDOSSEOUS HONEY COMB STIMULATION AND IMPLANT METHOD

Figure 4A:
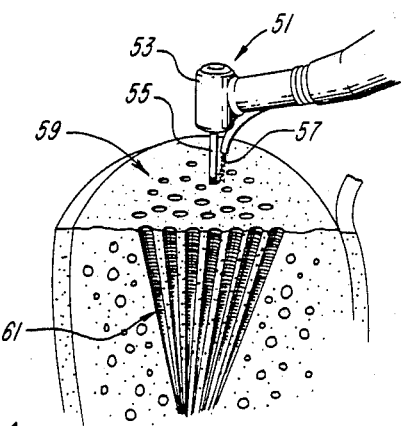
FIGS. 4A–4C are diagrammatic and cross sectional illustrations of the preparation of the site for the implant insertion, including a step of endosseous honeycomb stimulation followed by preparation of the cavity after a time lag for bone softening, followed by the insertion of the implant into the softened bone structure.

Referring to FIG. 4A, the site for the implant may be prepared through the utilization of a water cooled, high-speed drill illustrated by reference character 51. Here the head of the drill 53 is provided with a drill bit 55 or surgical burr, with a water spray or coolant spray being illustrated diagrammatically at 57. Initially, the site is prepared by lifting an access flap to uncover the bone structure at which the implant is to be inserted. The exposed bone here illustrated at 59 is drilled in a conical pattern diagrammatically illustrated at 61, with a typical depth of drill penetration being slightly less than the longitudinal dimension of the implant. The reason that the depth of the drilling is less than the length of the implant is that the osteoclassic process will provide softened bone to a deeper extent than the length of the inserted drill. As to the top surface area to be drilled, typically, for a 5 millimeter diameter implant, the top surface area which is to be drilled has a diameter of about twice the diameter of the implant, or 10 millimeters. Each tubular drilled hole is separated from an adjacent tubular drilled hole by approximately 1 to 1.5 millimeters, with the angle subtended by the honeycomb structure provided by the drilling being on the order of 15 to 20 degrees. Alternatively, straight drilling is permitted, with the drilling angle not being particularly significant. What is important however is that the surface of stimulation exceeds the circumference of the implant so that sufficient softened bone is provided within the site to provide correct seating of the implant, surrounding by stimulated bone. Depending on the bone density, either spongeous or cortical, a period of respectively three to five weeks is provided for sufficient softening of the bone structure.

Figure 4B:
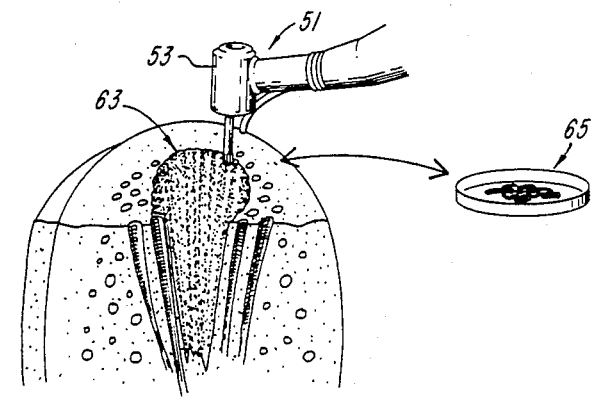

After sufficient softening has occurred, the implant site is prepared as illustrated in FIG. 4B through removal of softened bone material in a central area generally indicated by reference character 63, which preparation may be by drilling with a surgical burr or by scooping with an excavator, with softened bone to be kept aside in a dappen dish 65. Purpose of providing the removed material in a dish is to be able to provide softened bone material should the implant be somewhat smaller than the area opened up during this preparation step. The softened bone is therefore available to close up the gaps between any inserted implant and the surrounding structure at the recipients site.

Figure 4C:
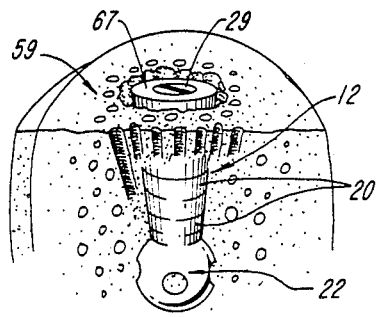

As illustrated in FIG. 4C, implant 12 is forced into the recipient site containing the softened bone material. The implant is pressed into the site such that the top portion 67 of the implant is submerged below the bone level. This will be more thoroughly described in connection with FIG. 5A. It will be appreciated that plastic screw 29 is inserted in a tapered orifice at the top of the submerged implant so as to prevent tissue growth into the threaded portion of the implant, which threaded portion is to receive the threaded screw protruding downwardly from the clinical cap or abutment to be affixed thereto after the initial healing period. This procedure provides automatic sizing of the implant site to the implant without expensive drilling equipment and provides for better implant retention for whatever implant may be used. Thus the subject site preparation technique is applicable not only to the subject implant, but rather may be used independently with any implant.

BONE GUIDING THROUGH IMPLANT

Referring now to FIG. 5A, implant 12 is submerged below bone level 60 such that, upon initial raising of a flap 62 of gingiva and preparation of the recipient site as described above in connection with FIGS. 4A–4C, it will be appreciated that the implant is implanted within softened bone structure 64 below the bone rim to counteract the loss of the bone rim due to the surgical management of the site. It will be noted that there is significant blood vessel activity as illustrated by vessels 66 surrounding the implant, which blood vessels play an important part as will be described in connection with FIGS. 5B, 5C, and 5D to provide sustenance to the ingrowth of new bone after osteoclasia has occurred. Note, ankylosis occurs at the bone/bone interface as indicated by double-ended arrow 71, whereas osseointegration is bone-to-titanium adhesion as shown at double-ended arrow 73.

Referring now to FIG. 5B, flap 62 is shown sutured to its adjacent material. At this juncture ankylosis starts and osteoclasia follows with the ingrowth of vessels 66 into the captured bone rings 34 or channels 32. This process takes place over the first 11 or so days. As can be seen, the bone particles in the rings are denser and of greater hardness than surrounding the bone 64. Thus, the recipient site bone is induced to remove the bone rings via osteoclasia followed by bone genesis. This results in the replacing of the bone rings with live bone for anchoring the implant into position as illustrated in FIG. 5D.

With respect to FIG. 5B, ankylosis occurs which is the binding of the live bone to the bone rings at the surface thereof. This is followed by the aforementioned osteoclasia in which there is a debridement of the bone particles within the rings, which complete debridement is illustrated in FIG. 5C. Note, further ingrowth of the vessels provides the nutrient source for the beginning growth of live bone from the surrounding live bone material.

As can be seen from FIG. 5D, one of the features of the Subject Invention is that during the initial implant healing period, live bone as illustrated by live bone particles 70 completely invade the implant structure to anchor the implant structure to the live bone exterior to the implant. This provides through growth of live bone replacing the dense, cortical-bone which is utilized to stimulate the entire process. This stimulation or inducement distinguishes the subject process over those implants which merely provide interstices or indents into which bone growth is supposedly to occur. It has been found that bone growth rarely occurs without some kind of stimulation which is provided in the Subject Invention by the interstitially clamped and held bone material whether or not the bone material extends completely through the implant. It will be appreciated that the prior references cited above which have interstices have no such stimulating material or if they do have bone within the implant it is loosely packed and therefore prevents any kind of osseointegration due to the unwanted generation of connective interstitial tissue. As mentioned hereinbefore, with any kind of loose particle configuration of bone, the process of osseointegration is prohibited due to the aforementioned formation of dense capsules of connective tissue surrounding the bone particles which are loosely packed. The process of implantation and initial healing with the covering of gingival flap, takes place on the order of one to two months.

EPITHELIAL DOWNGROWTH PREVENTION

Figure 5E:
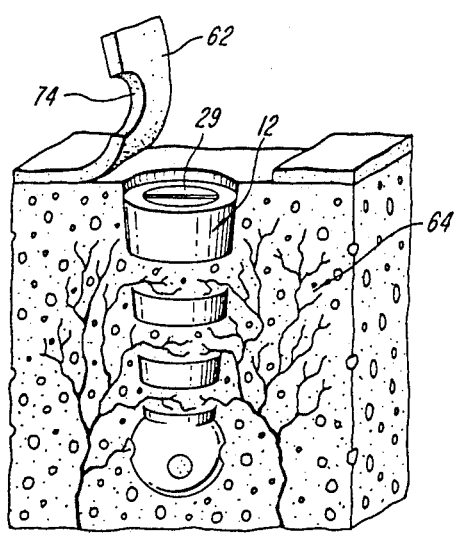
FIGS. 5E–5G illustrate a re-entry procedure in which an abutment or clinical cap is affixed to the implanted substructure, with FIG. 5E illustrating the removal of the gingival flap at the site of the implant and the provision thereof with a through-hole through the gingiva, with FIG. 5F illustrating the insertion of the abutment and the securing thereof to the substructure implant, and with 5G illustrating the placement of the semiporous ring of material about the abutment for the purpose of preventing epithelial downgrowth.

After stabilization of the implant through the above osteointegration, whether or not osseointegration has occurred, the original gingival flap 62 is removed from the site of implant 12 as seen by the lifting of the flap from this site in FIG. 5E. It will be appreciated that an aperture 74 is provided in flap 62 to accommodate the protrusion of an abutment therethrough as will be subsequently described. Here it can be seen that the original implant carries large plastic screw 29 to prevent tissue downgrowth which would otherwise occur and which would prevent adaptation of abutments to the initial implant.

Figure 5F:
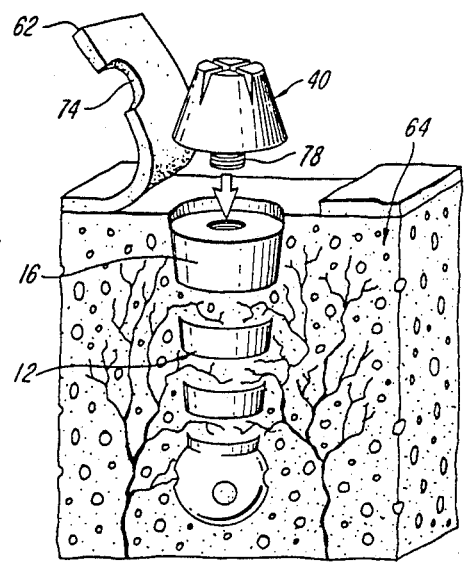

As seen in FIG. 5F, abutment 40 is presented to be fit to the top portion 16 of implant 12, with the screw 29 having been removed. Here it can be seen that abutment 40 is provided with a downward projecting screw portion 78 which is tightened down onto the top portion of the implant.

Figure 5G:
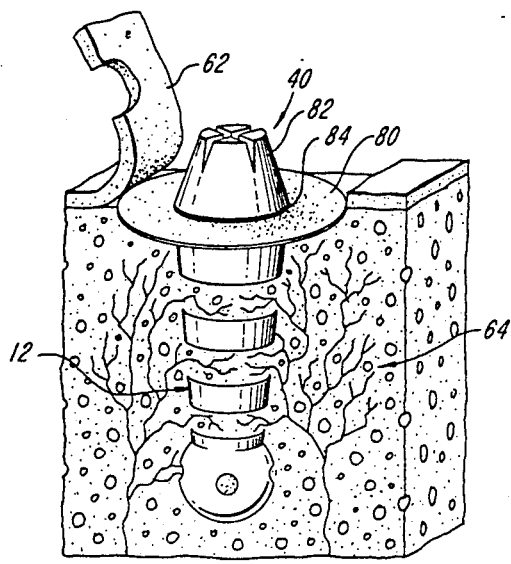

Referring now to FIG. 5G, abutment 40 is surrounded a ring 80 of semiporous material such as provided by a Millipore type filter ring or a ring of Gore-Tex material. The purpose of the semiporous structure is to allow connective tissue associated with healing to grow without resulting in epithelial down growth at the implant site. It will be appreciated that ring 80 has an aperture therethrough which is sealed to the surface 82 of the abutment 40 via an adhesive 84 of an adequate nature to secure close adaptation of the ring to the abutment and to the bone structure.

Figure 5H:
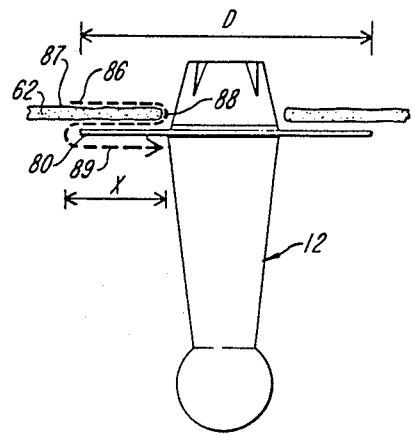
FIG. 5H is a diagrammatic illustration of the effect of the utilization of the semiporous ring of FIG. 5G, with the ring size dictating the ingrowth of epithelialization on and about the ring, thus retarding epithelial migration as osseointegration and osteointegration continues.

Note, that the adaption of such a filter or ring of material is to prevent epithelial downgrowth for a sufficiently long period of time to permit the healing and stabilization of the implant. As discussed hereinbefore, epithelial downgrowth provides for increased mobility of the implant under normal circumstances. Where epithelial downgrowth is to occur, osseointegration would be prevented at the top portion of the implant, thereby defeating the purpose of the stabilization of the implant with osseointegration. How epithelial downgrowth is controlled is illustrated diagrammatically in FIG. 5H in which implant 12 is shown having a ring of material 80 of diameter D, with a portion of the ring extending laterally a distance X from the implant. This distance may be on the order of 3 to 15 millimeters depending on the length of time it is desired to prevent epithelial downgrowth. It will be appreciated that epithelium grows at a rate of ¼ millimeter per day. This growth can be seen by dotted line 86, in which epithelium starts to grow from the top surface 87 of the gingival tissue 62 around the end 88 of the gingival tissue, and around the ring as illustrated at 89. It is important therefore that this growth of epithelium be retarded so that osseointegration continues at the top portion of the implant. Thus the utilization of such a semiporous ring or filter prevents epithelial downgrowth at the region adjacent the top portion of the implant until such time as sufficient stabilization of the implant can occur not only via osseointegration but also by the subject osteointegration.

While this invention relates to osteointegration and the securing of the implant through the generation of the new bone growth through the implant, it will be appreciated that the aforementioned ring is of utility in the Branemark system in order to provide for increased stabilization during the initial forty days. It will therefore be appreciated that the subject utilization of a ring of semiporous material may be used either with the subject clamped-bone implant or with other types of implants to prevent the ill effects of epithelial downgrowth. It will also be appreciated that the subject semiporous ring may be utilized regardless of the exterior configuration of the implant such that the implant need not, for instance, have the bulbous structure illustrated in FIGS. 5A–5H. It will therefore be appreciated that the utilization of the semiporous ring is an aid to virtually any type of implant expecting osseointegration. Note also that the ring may be replaced by resorbable material such as used for resorbable suture material.

RING REMOVAL

Figure 5I:
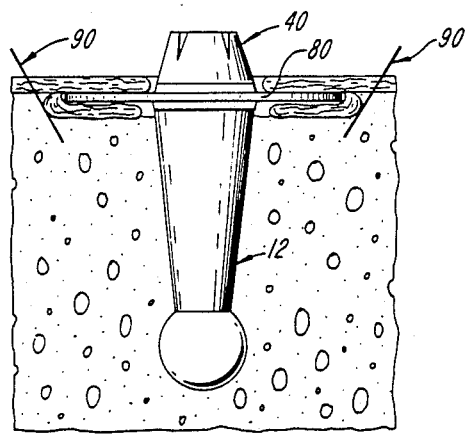
FIG. 5I is a diagrammatic illustration of epithelial downgrowth occurring and stopping at osseointegration at the surface of the implant, also showing the pre-ring removal and cutting lines for preparation of the site prior to ring removal.
Figure 5J:
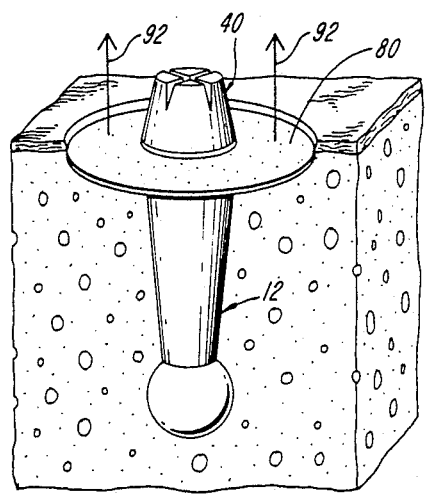
FIG. 5J is a diagrammatic illustration of that which is done to remove the semiporous ring.
Figure 5K:
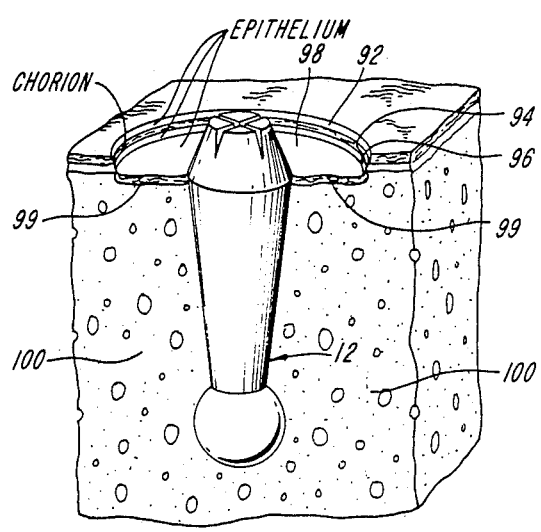
FIG. 5K is a diagrammatic illustration of the resultant site configuration after the removal of the semiporous ring of 5J.

Referring to FIG. 5I, upon initial stabilization of the implant and provision of the semiporous ring, after 40–45 days, the site is prepared as follows:

Cuts 90 are made through the gingival overlap of the ring in such a manner that the angle and position of the cut is such as to permit removal of the ring 80. As illustrated in FIG. 5J, upon exposure of the ring 80, it is removed in the direction of arrows 92 to provide, in one embodiment, the structure illustrated in FIG. 5K, in which an upper layer of epithelium 92 is exposed at the cut followed by a chorion ring 94 followed by epithelial surface 96, with epithelium 98 contacting implant 12 as well as resting on a tissue layer 99, which covers bone 100. It will be appreciated that since epithelial downgrowth is limited through the utilization of the ring, there is only minimal sulcular depth around and about the implant. This limits bacterial invasion around the implant shaft and enhance osseointegration.

OPTIONAL STABILIZATION

Figure 5L:
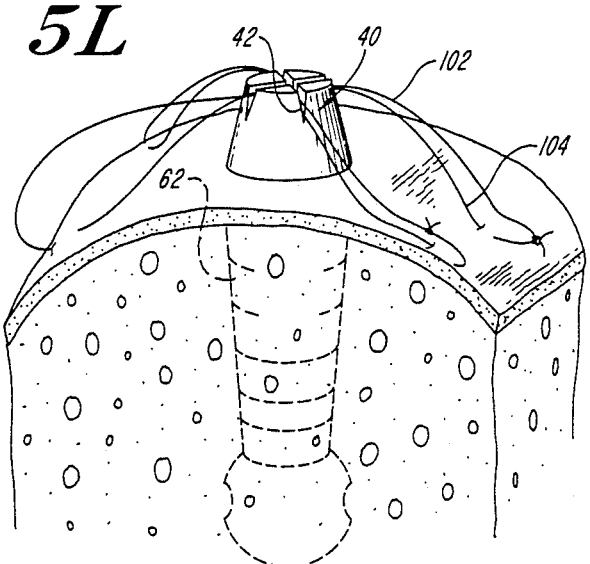
FIG. 5L is a diagrammatic illustration of an optional procedure for immobilizing the implant in position illustrating a net-type suturing procedure in which sutures criss-cross the abutment or clinical crown.

Referring now to FIG. 5L, optionally, after the aforementioned ring has been inserted and flap 62 has been secured over the implant and about the protruding abutment 40, the implant may be further stabilized with a basket type suturing procedure in which sutures 102 and 104 are sutured across the top portion of abutment 40 through the slots 42 provided therein. The purpose of the utilization of the sutures is to provide increased stabilization of the substructure implant during the healing period and also to prevent untoward side effects, for example tongue habits contacting the protruding abutment or any superstructure thereon. It will be appreciated that the sutures are to be in place between ten and fifteen days and aid in the success in the above-identified procedure.

CAP STRUCTURE

Figure 5M:
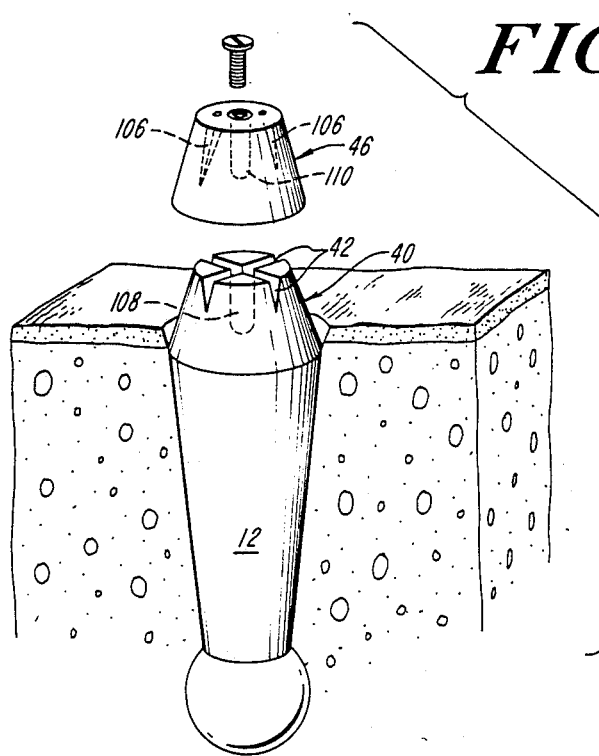
FIG. 5M is a diagrammatic illustration of the implant and its clinical crown in position, illustrating the superstructure to be cemented or otherwise affixed to the abutment after sufficient healing and immobilization of the implant has occurred.

Referring to FIG. 5M in this diagrammatic illustration, implant 12 has abutment 40 provided with the aforementioned cap 46 which is provided with internal ribs here illustrated in dotted outline by reference character 106 which mate with the slots 42. As seen in this figure in dotted outline abutment 40 is provided with a central core orifice 108 into which projects a mating centrally aligned pin structure 110 of cap 46. Not only do ribs 106 mate with the slots 42 described above, additionally structural rigidity and orientation is provided by the mating of the downwardly projecting central pin 110 into orifice or channel 108. This structure is more completely described in connection with FIG. 5N shown in exploded and cross sectional view.

Figure 5N:
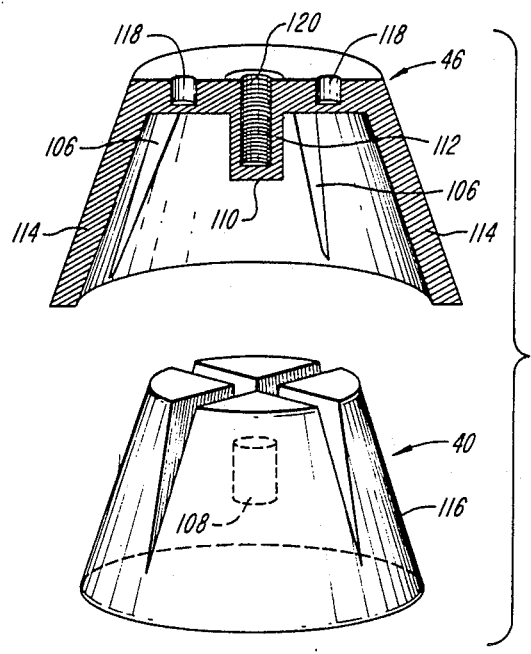
FIG. 5N is a cross sectional, exploded and diagrammatic view of the cap of FIG. 5N.

Referring now to FIG. 5N, it will be seen that abutment 40 is provided with the aforementioned central orifice or channel 108 which opens at the juncture of the base of the grooves. The downward projecting pin 110 is shown to have an internal threaded structure 112, the purpose of which will become apparent in FIGS. 9A-9C for the removal of the superstructure from the abutment. Here ribs 106 are shown projecting interiorally of cap walls 114, which cap is secured either by adhesive or other means to surface 116 of abutment 40. It will be noted in this figure that sealed apertures 118 are provided adjacent orifice 120 in downwardly projecting pin 110, such that any superstructure over cap 46 can be secured to the cap without the possibility of invasion through these orifices which will be described later. The purpose of the orifices 118 and 120 will be described hereinafter and relate to the facile removal of the cap from the abutment. It is extremely important that caps be removeable from abutments in an easy way in which the implant is not endangered. Removal may be necessary because of structural damage, or revamping, or abradement or damaging of the acrylic superstructure which occurs from time to time.

With respect to the abutment, visa vis the cap or crown which is to go on top of it, it will be appreciated with the use of adhesives there is to be some area left for the adhesive to flow to when the adhesive-laden cap is pressed onto the abutment. It is therefore desirable to have what is known as an internal vent within the system which as shown in FIG. 9A involves the utilization of the cavities within the crown, along with chamfered margins on the abutment to permit the outflow of adhesive. This adhesive is, of course, the excessive adhesive which may inadvertently be applied during the capping procedure.

OSTEOINTEGRATION VS OSSEOINTEGRATION

Figure 6:
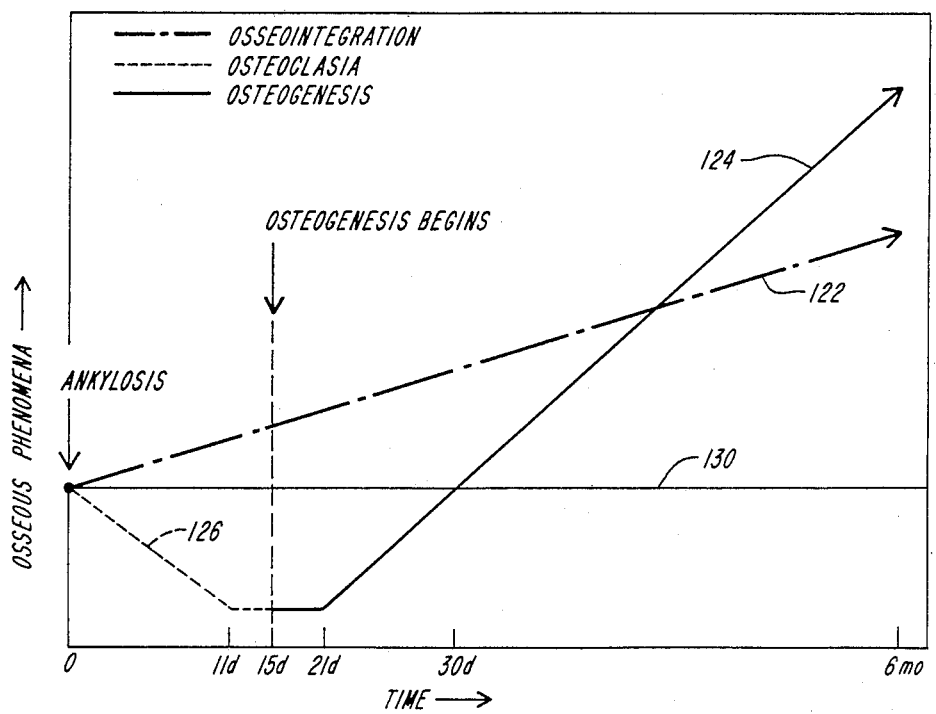
FIG. 6 is a graph illustrating the osseointgration, osteoclasia, and osteogenesis which occur over the time periods illustrated.

Having described two processes one osseointegration and the other osteointegration, or osteogenesis, the graph Presented in FIG. 6 illustrates typical time periods for the operation of both phenomena. As can be seen by dotted line 122, osseointegration, if it occurs at all, occurs from the initial implant through a period of approximately six months. Osteoclasia which is preceded by initial ankylosis occurs typically within a four to eleven day period, with osteogenesis beginning somewhere between the fifteenth day and the twenty first day. As can be seen from the graph and as illustrated by the solid line 124, osteogenesis starts out at a relatively slow pace and then rapidly increases its activity as indicated by the slope of line 124. As will be seen by dotted line 126, the osteoclasia which precedes immediately after ankylosis has an activity which is relatively rapid, which is then followed after a brief period by a relatively rapid osteogenesis. What this graph shows is that sufficient stabilization can occur in as little as thirty days as indicated by the crossing of solid line 124 with coordinate 130. It will also be appreciated that osteogenesis continues at a relatively rapid rate as compared with osseointegration even after sufficient stabilization has occurred. This is primarily due to the structure in which bone is guided through the implant as opposed to relying on a pure surface contacting technique presented by osseointegration. The graph, of course, also shows that both processes may take place simultaneously. However, as pointed out hereinbefore, whether or not osseointegration takes place, osteogenesis or osteointegration results in sufficient stability within a relatively short period of time so as to permit temporary prosthesis to be inserted.

UNITARY IMPLANTS

Figure 7:
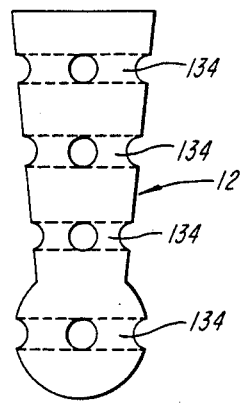
FIG. 7 is a diagrammatic illustration of a further embodiment of the subject implant illustrating a unitary implant structure, with channels or through holes being drilled or otherwise provided completely through the implant structure.

Referring now to FIG. 7, it will be appreciated that one embodiment of the Subject Invention implant 12 may be a unitary structure provided with through-hole channels 134 going in a variety of directions. It is preferable that this implant be made of pure titanium and be packed as solidly as possible with dense or cortical bone. The bone may be press fit into the implant to such an extent that adhesives are not necessary. However, adequate compatible adhesives are available to immobilize the dense bon within the implant with or without the dove tailed structure mentioned hereinbefore.

BULB STRUCTURE

Figures 8A, 8B:
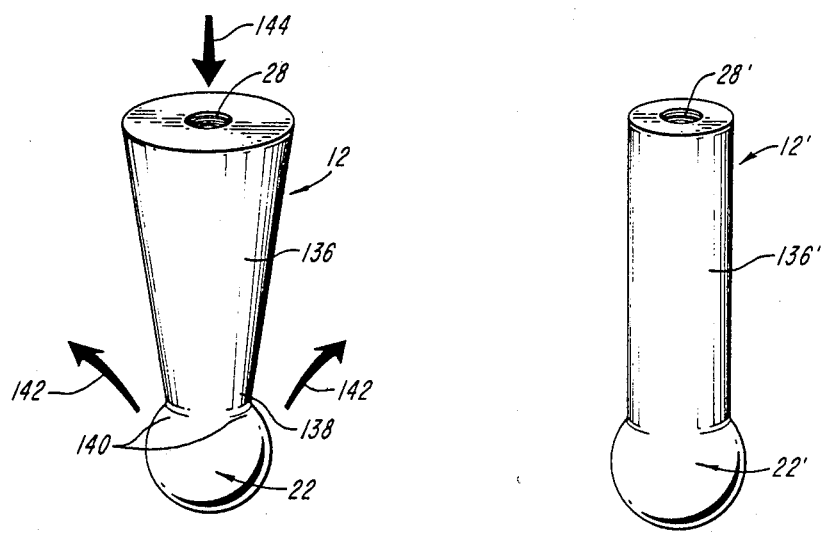
FIGS. 8A and 8B are diagrammatic illustrations of an implant structure showing a bulbous bottom end for stress relief for either tapered or straight implants, which may be used either with the subject pure titanium/bone system or with any compatible implant material, the purpose of which is to provide initial stress relief during implantation and subsequent stress release during usage.

Referring now to FIG. 8A, it will be appreciated that regardless of whether bone is immobilized within an implant structure, the implant may take on the structure illustrated in FIGS. 8A or 8B in that a bulbous end 22 is provided for the aforementioned stress relief. In FIG. 8A the implant is tapered, with the diameter of a shaft 136 of implant 12 being narrower at its base here illustrated by reference character 138 to provide that when a bulbous structure is utilized rather than merely rounding the end of an existing structure, a bulbous structure prevents upward movement of the implant by virtue of the top surfaces of the bulb here illustrated by reference character 140 such that motion in the direction of arrows 142 is inhibited. Likewise the bulbous nature of the structure prevents forces of a downward nature illustrated by reference character 144 from being effective in moving the already stabilized implant. Referring to FIG. 8B, the implant 12' sides 136' may be straight with a larger diameter bulb 22' at the bottom.

LATERAL IMPLANTATION

It will be appreciated that while vertical implantation has been described hereinbefore, lateral implantation is possible with the subject technique, honey comb endosseous stimulation which permits the insertion of the bulbous end within the softened structure of the bone.

Lateral insertion of course implies that a lateral flap is raised and that the techniques described hereinabove are applied laterally as opposed to vertically.

CAP REMOVAL

Referring now to FIG. 9A, assuming removal of a crown or other superstructure shown in dotted outline 121 from cap 46, it will be appreciated that cap 46 is provided with the aforementioned tapped pin 110 in which originally a plastic screw 122 is placed prior to the tooth or the superstructure being adhered thereto by the serrated surface 56. Here it will be seen that cap 46 is provided with internal adhesive receiving orifices or channels 124 which receive excess adhesive 126, which excess adhesive flows into these channels when cap 46 is adhered to abutment 40. Further, abutment 40 is chamfered as illustrated at 126 to permit the outflow of adhesive shown at 128 upon the adhering of the cap to the abutment.

Also shown is the fact that pin 110 is somewhat shorter than orifice 108 which provides an adhesive well 130 at the base of pin 110, with excess adhesive also flowing into this well as indicated by arrows 132.

Orifices 118 in the top surface 134 of the cap are filled in one embodiment with rubber inserts 136 which rest upon a frangible or breakable thin unitary portion of the cap here illustrated at 140. The purpose of which will be described in connection with FIG. 9B.

Referring to FIG. 9B and for purposes of removal of cap 46 from abutment 40, a tool generally indicated by reference character 142 is provided with a base 144 which carries a loosely held bolt 146 adapted to replace screw 122 of FIG. 9A, such that bolt portion 148 may be threaded into threaded orifice 112.

Depending downwardly from base 144 are pins 150 which are adapted to be inserted into orifices 118 which are shown in FIG. 9B as having rubber or other inserts removed therefrom, thereby exposing breakaway portions 140. In order to expose the inserts in 118 and the top surface of cap 46, the top portion may be abraded away as indicated by dotted line 152. As will be seen from this Figure, pins 150 are adapted to the pressed down into orifices 118 upon the screwing down of device 142 over top of cap 46.

Figure 9C:
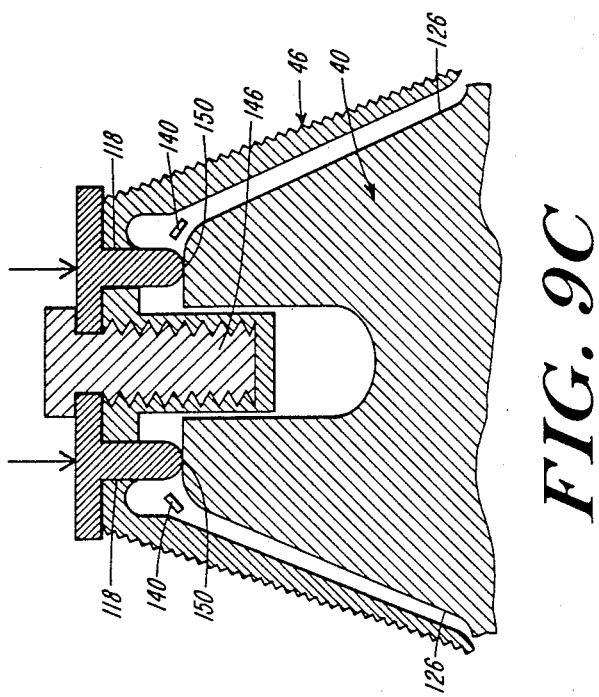

Referring now to FIG. 9C, it will be seen that upon the screwing down of a bolt 146, pins 150 contact the top surface of abutment 40 such that cap 46 is moved upwardly as bolt 146 is screwed down, due to the projection of pins 150 through the now opened orifices 118, with breakaway portions 140 being removed as indicated.

It will be appreciated that this manner of removing of a cap from an abutment is exceedingly simple with, the cap initially being sealed at its top via the aforementioned rubber inserts and the breakaway orifice bottoms such that liquid cannot pass from the top portion of the cap to the bottom.

Upon removal, however, the pins break through the breakable bottoms after removal of the rubber inserts, with the pins serving to work against the top portion of the abutment to move cap 46 upwardly from abutment 40 as illustrated in FIG. 9C.

IMPLANT REMOVAL

Figure 10:
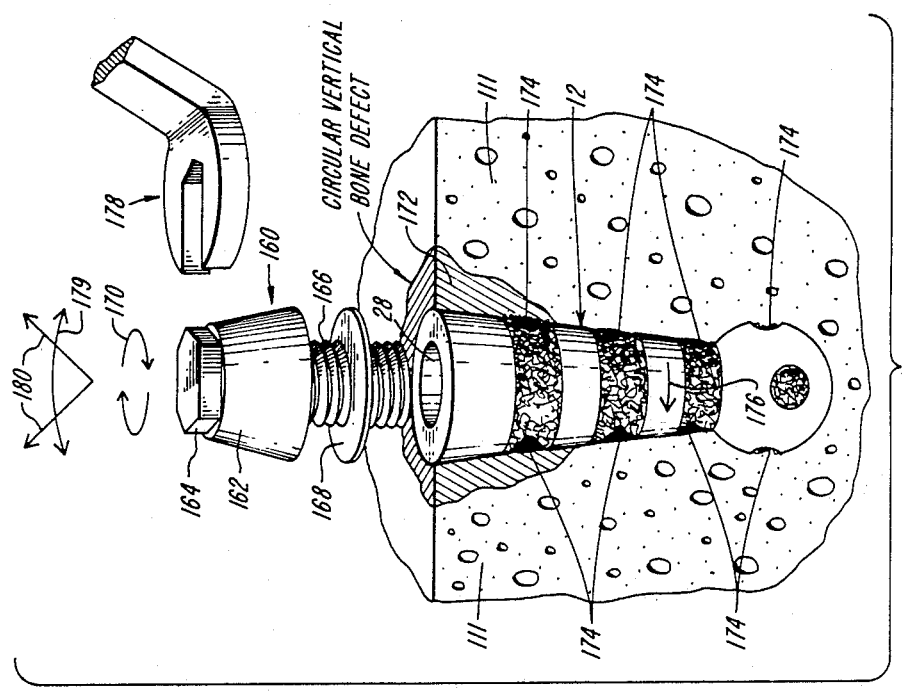

Referring now to FIG. 10, insert 12 may be removed from the bony structure 111 through the utilization of a cap generally indicated by reference character 160 including a base 162 and a hex or other head portion 164, with a bolt or screw portion 166 depending downwardly therefrom and carrying a lock 168 thereon. Device 160 is adapted to be screwed into threaded orifice 28 at the top of the implant such that when screwed into place in a clockwise direction as indicated by arrows 170, cap 160 is virtually immovably secured to implant 12.

It will be appreciated that implants are removed for a variety of circumstances, one common circumstance being the circular vertical bone defect shown to occur in region 172. Because of the tight hold to the implant with the aforementioned osteointegration or osteogenesis, it is extremely difficult to remove the implant even when circular vertical bone defect is extensive. It is therefore necessary to break the guided through bone at points illustrated by reference character 174 at the exterior surface of the implant. In order to do this, once the cap 160 is screwed down into the implant it is further screwed clockwise as illustrated by arrow 176 with a quick twist given to the top portion or hex head 164 via a suitable vice grip type plyers or forceps 178, thereby to cause the bone breakage at the points in which the bone has grown through implant 12. Upon a quick twist in the clockwise direction, the cap is wiggled or maneuvered in the directions illustrated by arrows 179 and 180 so as to wiggle the implant free of its original implanted position, first by a quick twist along its longitudinal axis, followed by wiggling in any direction through the utilization of forceps or pliers 178.

The subject removal cap is therefore important, especially with implants of the through-bone type, due to the increase holding power of these types of implants as opposed to other of implants. It will however be appreciated that such a device locked onto the top of any type of implant will be useful in the removal of an implant from the surrounding bone structure.

While it will be appreciated that clockwise motion has been utilized to secure the cap to the implant, for those implants that screw into the bone in a threaded clockwise direction, the screw or bolt on the cap may be threaded counter clockwise for tightening such that not only will the cap be secured to the implant in a direction countered to the screwing in of the implant, but it will also cause the implant to rise up due to its threaded nature, breaking any bond between the implant and the surrounding bone as the implant is unscrewed. Furthermore, the implant of FIG. 2 being dismantable, the implant may be re-vamped and reutilized if need be.

Having above indicated a preferred embodiment of the present invention, it will occur to those skilled in the art that modifications and alternatives can be practiced within the spirit of the invention. It is accordingly intended to define the scope of the invention only as indicated in the following claims

I claim:

1. A dental implant having a shaft and a bulbous end attached thereto, with the bulbous end having a diameter greater than the remainder of the shaft to which it is attached, said implant having tightly captured bone channelled substantially through the implant, a portion of said bone being exposed at a surface of said implant for stimulating osteointegration through the guiding of new bone growth into said implant so as to provide more than surface attachment to said implant, said implant providing a mechanical anchoring via bone growth through said implant.

2. The implant of claim 1 wherein said implant is of pure titanium, thereby to permit implant stabilization by osseointegration as well as osteointegration.

3. The implant of claim 1 wherein said implant includes passageways from one side thereof to another and wherein said captured bone is provided in said passageways.

4. The implant of claim 1 wherein said implant includes members having dove tailed surfaces for securing said captured bone thereto.

5. The implant of claim 1 wherein said captured bone is compacted lyophilised or freeze dried bone.

6. The implant of claim 5 wherein said bone is dense cortical bone.

7. The implant of claim 1 wherein said implant includes a tapered shaft and further includes a bulbous bottom portion thereon.

8. The implant of claim 1 wherein said implant includes a bulbous bottom portion.

9. The implant of claim 1 wherein said implant has straight cylindrical sides and a bulbous end portion.

10. A dental implant having tightly captured bone channelled substantially through the implant, a portion of said bone being exposed at a surface of said implant for stimulating osteointegration through the guiding of new bone growth into said implant so as to provide more than surface attachment to said implant, said implant providing a mechanical anchoring via bone growth through said implant, said implant including a head portion and a central threaded portion, with intermediate titanium portion secured to said central threaded portion, said titanium implant having a bulbous bottom portion with said bone being captured inbetween said intermediate portions and said head portion and inbetween the lowest. Intermediate portion and said bottom bulbous portion.

11. The implant of claim 10 wherein said bottom portion includes a split sphere structure having bone captured between the split portions of said sphere.

12. The implant of claim 11 wherein the bottom of said head portion and top and bottom of an intermediate portion as well as a top portion of said bottom bulbous portion are doved tailed, thereby to retain said captured bone tightly within said implant.

13. Apparatus for decoupling a cap from an abutment attached to a dental implant comprising:
a fixture including a base having a downwardly-projecting free moving bolt therethrough and a number of downwardly-projecting pins to either side of said bolt,
said cap including a screw threaded portion adapted to receive said bolt, and having orifices to either side of said bolt adapted to receive said pins therethrough, whereupon tightening of said bolt in said screw threaded portion provides a downward movement of said pins through respective orifices in said cap, whereby said pins contact said abutment and press thereagainst such that said cap moves in an upward direction.

14. The apparatus of claim 13 wherein said orifices include frangible base portions dislodgeable by said pins, and are adapted to carry inserts, both said base portions and said inserts preventing the passage of liquids through said cap and into the area of said abutment.

15. A method for securing implants within a mandibular or maxillary bone, comprising the steps of
uncovering the portion of the bone at the site at which the implant is to be placed;
drilling a large number of small diameter holes into the implant site;
waiting for a sufficient time for osteoclasia to provide softened bone structure into which an implant can be forced, and;
forcing an implant into the softened bone area so that the implant is inserted therein, whereby the holes drilled need not be sized to the implant, and whereby the implant is more securely held in place due to the softened bone structure which tightly surrounds and contacts the entirety of the implant.

16. The method of claim 15 wherein said implant is forced below the surface of the bone, thereby to permit stabilization of the top of the implant via osseointegration.

17. The method of claim 15 and further including the step of using fluid-cooling during the drilling step.

18. The method of claim 15 and further including the step of excavating softened bone material at the implant site, prior to implant insertion.

19. The method of claim 15 wherein said drill pattern is a honey comb conical pattern.

20. The method of claim 15 wherein the pattern of drilled holes at the bone surface occupies a larger area than the maximum cross sectional area of the implant.

21. In a method of stabilization of an implant which has been inserted into a maxillary or mandibular bone, the step of placing a flap of material over the implant such that the material surrounds the implant for retarding epithelial downgrowth, said material permitting air flow therethrough, said material being placed at the top portion of the implant and overlying the surrounding bone area, said material retarding epithelial downgrowth by providing a lateral path for epithelialization prior to downgrowth, thus to prevent downgrowth for a predetermined period of time based upon the distance between the implant and the outer edge of said material.

22. The method of claim 21 wherein said material is semiporous.

23. The method of claim 21 wherein said implant includes an upwardly protruding abutment, and wherein said material is in the form of a ring placed over said abutment.

24. The method of claim 23 wherein said ring is secured to said implant by adhesive means.

25. The method of claim 21 wherein said material is either a filter material or a Gore-Tex material, to allow breathing through the material for the tissue growth.

26. The method of claim 21 wherein said material is resorbable.

27. A method for providing an improved stabilized dental implant comprising the steps of:
providing a dental implant having a shaft and a bulbous end attached thereto, with the diameter of the bulbous end being greater than (the remainder) of the shaft to which the bulbous end is attached, said implant having compacted bone at least partially therethrough, said bone being immobilized from movement; and,
inserting said implant into a prepared cavity within a mandibular or maxillary bone structure, such that osteointegration occurs, thereby guiding new bone from one side of the implant into the implant for increased stabilization of the implant through the stimulus afforded by ankylosis followed by osteoclasia as the densely packed bone is debrided and replaced with new bone.

28. The method of claim 27 wherein the initial packed bone runs from one side of the implant to the other, thereby stabilizing the implant through the formation of new bone from one side of the implant to the other side of the implant.

29. The method of claim 31 wherein said dental implant is secured to the surrounding bone through osteointegration whereby healing time is reduced.

30. The method of claim 29 wherein said healing period is reduced to as little as one month through the osteogenesis occurring at said implant.

31. The method of claim 30 wherein osteointegration is made to occur through the ankylosis, followed by osteoclasia followed by osteogenesis.

32. The method of claim 31 wherein said ankylosis and osteoclasia is made to occur through the utilization of packed bone running into said implant with a portion of said packed bone being exposed at the surface of said implant, said bone being compacted so as to be immovable and in close contact with itself, thereby to stimulate said osteoclasia followed by osteointegration.

33. The method of claim 29 and further including providing osseointegration through the utilization of a pure titanium metal for the implant, such that osseointegration occurs simultaneously with osteointegration, thereby to further reduce the healing time.

* * * * *